United States Patent
Chen et al.

(10) Patent No.: US 9,758,778 B2
(45) Date of Patent: Sep. 12, 2017

(54) POLY-L-LACTIC ACID (PLLA) MICROTUBE ARRAY MEMBRANE-IMMOBILIZED YEAST CELLS FOR BIOETHANOL FERMENTATION

(71) Applicants: TAIPEI MEDICAL UNIVERSITY, Taipei (TW); NATIONAL TAIWAN OCEAN UNIVERSITY, Keelung (TW)

(72) Inventors: Chien Chung Chen, Taipei (TW); Hong-Ting Lin, Keelung (TW)

(73) Assignees: Taipei Medical University, Taipei (TW); National Taiwan Ocean University, Keelung (TW)

( * ) Notice: Subject to any disclaimer, the term of this patent is extended or adjusted under 35 U.S.C. 154(b) by 0 days.

(21) Appl. No.: 14/968,450

(22) Filed: Dec. 14, 2015

(65) Prior Publication Data
US 2017/0166881 A1   Jun. 15, 2017

(51) Int. Cl.
*C12N 11/08* (2006.01)
*C12N 1/16* (2006.01)
*C12P 7/06* (2006.01)

(52) U.S. Cl.
CPC ............... *C12N 11/08* (2013.01); *C12N 1/16* (2013.01); *C12P 7/06* (2013.01)

(58) Field of Classification Search
None
See application file for complete search history.

(56) References Cited

U.S. PATENT DOCUMENTS 9,091,007 B2 *   7/2015   Chen .................. D01D 5/0069

OTHER PUBLICATIONS

Chen, Chien-CHung; et al; "Accelerated bioethanol fermentation by using a novel yeast immobilization technique: Microtube array membrane" Process Biochemistry, 50, 1509-1515, 2015.*
Mehaia, Mohamed A; Cheryan, Munir; "Ethanol production in a hollow fiber bioreactor using *Saccharomyces cerevisiae*" Applied Microbiology and Biotechnology, 20, 100-104, 1984.*
Inloes, Douglas S; et al; "Ethanol Production by *Saccharomyces cerevisiae* Immobilized in Hollow-Fiber Membrane Bioreactors" Applied and Environmental Microbiology, 46-264-278, 1983.*
Kang, Whankoo; et al; "Ethanol Production in a Microporous Hollow-Fiber-Based Extractive Fermentor with Immobilized Yeast" Bioengineering and Biotechnology, 36, 826-833, 1990.*
A.K. Chandel, M.L. Narasu, G. Chandrasekhar, A. Manikyam, L.V. Rao, Use of *Saccharum spontaneum* (wild sugarcane) as biomaterial for cell immobilization and modulated ethanol production by thermotolerant *Saccharomyces cerevisiae* VS3, Bioresour. Technol. 100 (2009) 2404-2410.
D.J. O'Brien, L.H. Roth, A.J. McAloon, Ethanol production by continuous fermentation-pervaporation: a preliminary aconomic analysis, J. Membr. Sci. 166 (2000) 105-111.

* cited by examiner

*Primary Examiner* — David Berke-Schlessel
(74) *Attorney, Agent, or Firm* — WPAT,P.C., Intellectual Property Attoneys; Anthony King; Kay Yang

(57) ABSTRACT

The invention uses a highly porous MTAM to immobilize yeast cells for bioethanol fermentation, a first in bioethanol production. The invention also optimizes the conditions to prepare MTAM-immobilized cells and evaluates their potential for batch bioethanol fermentation.

14 Claims, 3 Drawing Sheets

POLY-L-LACTIC ACID (PLLA) MICROTUBE ARRAY MEMBRANE-IMMOBILIZED YEAST CELLS FOR BIOETHANOL FERMENTATION

FIELD OF THE INVENTION

The invention relates to immobilized yeast cells used for fermentation. Particularly, the invention provides a renewable poly-1-lactic acid (PLLA) microtube array membrane (MTAM)-immobilized yeast cell and the application thereof in bioethanol fermentation.

BACKGROUND OF THE INVENTION

Fossil fuel prices and environmental concerns have driven a search for renewable energy sources. Bioethanol is a type of biofuel that can be produced through the fermentation of biomass. First-generation bioethanol production utilizes sugar and starch from crops as a feedstock. It encounters multiple challenges such as rising food prices and scarcity of arable farmland, resulting in an urgent need for alternative solutions. Third-generation bioethanol production uses algae and requires the biomass to be pretreated and hydrolyzed for saccharification as well as generation of fermentable sugars to be used by other microorganisms in order to produce bioethanol through fermentation. However, pretreatment and hydrolysis of biomass are often accompanied by the generation of inhibitors, which seriously impede subsequent microbial fermentation to produce bioethanol. Thus, the key challenges associated with this energy source are related to the ability to produce bioethanol more efficiently without competing for food crop supply and cultivable land.

Immobilization is a way to isolate or localize intact cells in a certain space and maintain their catalytic activity. Immobilized cells can effectively reduce the negative effects of inhibitors and the processing cost of inoculum preparation for continuous or fed-batch fermentation of microorganisms. Immobilization techniques can be categorized as follows: (1) immobilization on solid carrier surfaces, (2) entrapment within a porous matrix, (3) mechanical containment behind barriers, and (4) cell flocculation (aggregation). Bioethanol fermentation using immobilized cells can increase cell density, shorten fermentation time, increase ethanol and inhibitor tolerance, and improve the feasibility of using continuous fermentation, resulting in more efficient bioethanol production. When sodium alginate beads were used for immobilization with *Saccharomyces cerevisiae* for bioethanol fermentation, it was found that immobilized yeast cells converted glucose into alcohol more efficiently than free yeast cells during batch fermentation, and the beads immobilized with yeast cells could be reused for 5 consecutive batch runs. Moreover, using multihole sterile loofah sponges or cicada cocoons for *Kluyveromyces marxianus* immobilization enhanced ethanol fermentation compared with that using free cells. Furthermore, *S. cerevisiae* VS3 immobilized on rice straw boosted bioethanol fermentation and was reusable for 8 consecutive batch runs (A. K. Chandel, M. L. Narasu, G. Chandrasekhar, A. Manikyam, L. V. Rao, *Use of Saccharum spontaneum (wild sugarcane) as biomaterial for cell immobilization and modulated ethanol production by thermotolerant Saccharomyces cerevisiae VS3*. Bioresour. Technol. 100 (2009) 2404-2410).

The current techniques to immobilize cells have several drawbacks. The surface attachment of cells using chemical linking agents, such as glutaraldehyde, may be unsuitable for the production of ethanol or beverages. Moreover, because there are no barriers between solution and cells, cell detachment and relocation may contaminate products. Another approach to cell immobilization is using a porous gel matrix, such as Ca-alginate, to entrap cells and obtain high biomass loadings for fermentation; however, the bead structure can destabilize in the presence of acid or diffusion limited gases, such as $CO_2$ in ethanol fermentation, and result in bead rupture. Cell flocculation is considered a relatively low-cost method; however, the flocculation of some yeasts is inhibited by the presence of sugars, such as glucose, and ethanol. Using the method of containment behind a barrier, such as that used in microporous membrane filters, for cell immobilization is most suitable when a cell-free product is required. However, there are inherent problems such as possible membrane fouling, high cost, and container recycling issues (D. J. O'Brien, L. H. Roth, A. J. McAloon, *Ethanol production by continuous fermentation-pervaporation: a preliminary economic analysis*, J. Membr. Sci. 166 (2000) 105-111).

SUMMARY OF THE INVENTION

Alcoholic fermentation by yeasts converts one mole of sucrose into two moles of ethanol and two moles of carbon dioxide. Since $CO_2$ production during alcohol fermentation, the produced gases may disrupt the gel structure of the gel matrix-immobilized yeasts and thus cause a problem in stability of the gel-immobilized yeasts. The invention uses MTAM to immobilize yeasts and the immobilized yeasts used in alcohol fermentation have high stability and yield. The invention provides a combination of yeast cells and a porous microtube array membrane (MTAM), wherein the yeast cells are immobilized in the MTAM and wherein the yeast encapsulation efficiency is more than 60%. In some embodiments, the yeast encapsulation efficiency is more than 65%. In some embodiments, the yeast encapsulation efficiency is about 60% to about 75%, about 65% to about 75% or about 65% to about 70%.

In some embodiments, the yeast cell is *Kluyveromyces marxianus*, *Kluyveromyces lactis*, *Kluyveromyces lipolytica*, *Saccharomyces cerevisiae* or *Schizosaccharomyces pombe*.

In some embodiments, the MTAM is highly aligned and closely packed fiber assembly, wherein the fibers are packed together to form a single layer and the orientation of the fibers is no larger than +/−50. In one embodiment, the fibers can be hollow or solid. In some embodiments, the pore size of the MTAM ranges from about 20 nm to about 40 nm, about 25 nm to about 40 nm, about 30 nm to about 40 nm, about 20 nm to about 35 nm, about 20 nm to about 30 nm or about 28 nm to about 32 nm, in diameter. In some embodiments, the MTAM consists of biodegradable and/or bioabsorbable polymer.

The invention also provides a method for bioethanol fermentation, comprising the following steps:
(a) immobilizating about $10^7$ to about $10^9$ cell numbers (CFU/mL) of yeast cells in MTAM by in situ preparation or siphon preparation to encapsulate the yeast cells into the MTAM with more than 60% encapsulation efficiency; and
(b) fermenting a sugar with the resulting MTAM to produce ethanol by batch fermentation.

In some embodiments, the the cell number of the yeast cells is about $10^8$ CFU/mL; the sugar is glucose, fructose or sucrose; and the batch fermentation is repeated-batch fermentation.

DETAILED DESCRIPTION OF THE INVENTION

Figure 1:
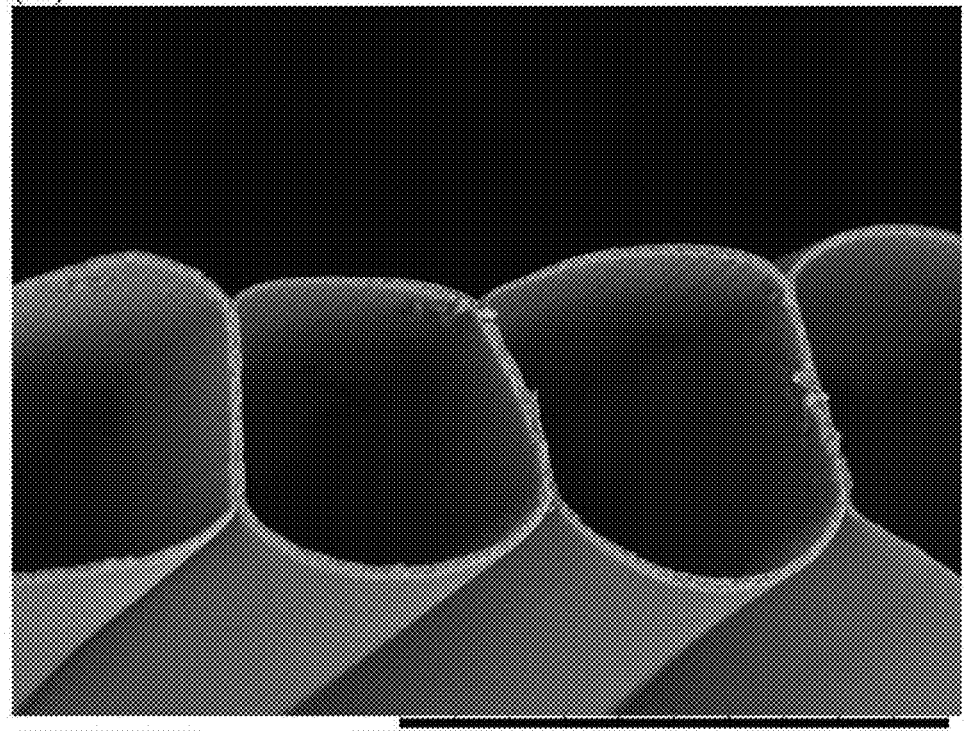
FIGS. 1 (a) to (c) show the SEM section image of (a) MTAM and the light microscopy images of (b) free *K. marxianus* and (c) MTAM-immobilized *K. marxianus* prepared by in situ method.
Figure 1:
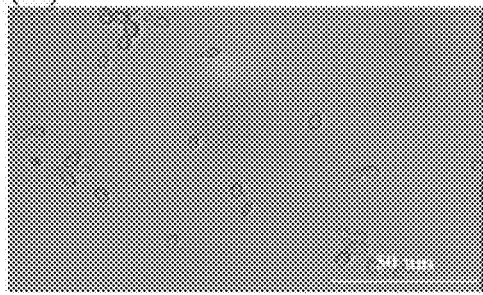
Figure 1:
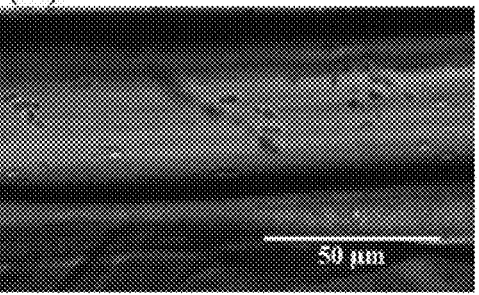

The invention uses a highly porous microtube array membrane (MTAM) to immobilize yeast cells for bioethanol fermentation. MTAMs serve as an excellent substrate to immobilize yeast for fermentation processes on an industrial scale.

Although many of the words, terms and titles employed herein are commonly used and conventionally understood within traditional medical and scientific contexts, summary descriptions and definitions of some terms and of particular names, designations, epithets or appellations are provided below. These descriptions and definitions are provided as an aid in recognizing and appreciating the true variety and range of applications intended for inclusion within the scope of the present methodology.

Throughout the description and claims of this specification, the word "comprise" and other forms of the word, such as "comprising" and "comprises," means including but not limited to, and is not intended to exclude, for example, other additives, components, integers, or steps.

As used herein, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "5" is disclosed, then "about 5" is also disclosed. It is also understood that when a value is disclosed, then "less than or equal to" the value, "greater than or equal to the value" and possible ranges between values are also disclosed, as appropriately understood by the skilled artisan. For example, if the value "5" is disclosed, then "less than or equal to 5" as well as "greater than or equal to 5" is also disclosed. It is also understood that throughout the application, data are provided in a number of different formats and that these data represent endpoints and starting points and ranges for any combination of the data points. For example, if a particular data point "5" and a particular data point "10" are disclosed, it is understood that greater than, greater than or equal to, less than, less than or equal to, and equal to 5 and 10 are considered disclosed as well as between 5 and 10. It is also understood that each unit between two particular units is also disclosed. For example, if 5 and 10 are disclosed, then 6, 7, 8, and 9 are also disclosed.

As used herein, the term "encapsulation" is the inclusion of one thing within another thing such that the included thing is not apparent. In the invention, "encapsulation" denotes that yeast cells are included within the porous microtube array membrane.

As used herein, the term "immobilization" denotes a substance attached to an inert, insoluble carrier.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymeric solution or melt provided from one or more needles, slots or other orifices is charged to a high voltage relative to a collection grid. Electrical forces overcome surface tension and cause a fine jet of the polymeric solution or melt to move towards the grounded or oppositely charged collection grid.

As used herein, the term "polymer" refers to and generally includes, but is not limited to, homopolymers, copolymers, such as, for example, block, graft, random and alternating copolymers, terpolymers, etc. and blends and modifications thereof. Preferably, it can include, but is not limited to, polylactides, polylactic acids, polyolefins, polyacrylonitrile, polyurethane, polycarbonate, polycaprolactone, polyvinyl alcohol (PVA), cellulose, chitosan nylon (e.g., nylon 6, nylon 406, nylon 6-6, etc.), polystyrene, proteins, and the like, or combinations thereof. Unless otherwise specifically limited, the term "polymer" is intended to include all possible geometrical configurations of the material. These configurations include, but are not limited to, isotactic, syndiotactic and random symmetries. Suitable solvents for each polymer can be selected from solvents known to those skilled in the art, including, but not limited to, sulfuric acid, formic acid, chloroform, tetrahydrofuran, dimethyl formamide, water, acetone, and combinations thereof.

As used herein, the term "nano-sized fibers" or "nanofibers" refers to very small diameter fibers having an average diameter not greater than about 1500 nanometers (nm). Nanofibers are generally understood to have a fiber diameter range of about 10 to about 1500 nm, more specifically about 10 to about 1000 nm, more specifically still about 20 to about 500 nm, and most specifically about 20 to about 400 nm. Other exemplary ranges include about 50 to about 500 nm, about 100 to 500 nm, or about 40 to about 200 nm. In instances where particulates are present and heterogeneously distributed on nanofibers, the average diameter of a nanofiber can be measured using known techniques (e.g., image analysis tools coupled with electro microscopy), but excluding the portions of a fiber that are substantially enlarged by the presence of added particles relative to the particle free portions of the fiber.

As used herein, the term "oriented fibers" indicates that substantially all fibers in a specific structure or array are arranged parallel to each other in a longitudinal direction ("unidirectionally oriented") or in a well-defined three-dimensional network ("three-dimensionally oriented"). In other words, the fibers are not randomly spatially arranged with respect to each other. In most instances, the fibers described herein grow in a generally perpendicular direction relative to the supporting substrate surface and there is very minimal, if any, branching of individual fiber strands.

As used herein, the term "single layer of material" or "single-layered material" refers to a material composed of a single layer which can be variable in thickness.

As used herein, the term "plurality of layers" or "multi-layered material" refers to a "stack" of single-layered materials.

In one aspect, the invention provides a combination of yeast cells and a porous microtube array membrane (MTAM), wherein the yeast cells are immobilized in the MTAM and wherein the yeast encapsulation efficiency is more than 60%. Preferably, the yeast encapsulation efficiency is more than 65%. More preferably, the yeast encapsulation efficiency is about 60% to about 75%, about 65% to about 75% or about 65% to about 70%.

In some embodiments, the yeast cell is *Kluyveromyces marxianus*, *Kluyveromyces lactis*, *Kluyveromyces lipolytica*, *Saccharomyces cerevisiae* or *Schizosaccharomyces pombe*. Preferably, the yeast cell is *K. marxianus*.

In some embodiments, the MTAM is a highly aligned and closely packed fiber assembly, wherein the fibers are packed together to form a single layer and the orientation of the fibers is no larger than +/−50. In one embodiment, the fibers can be hollow or solid. Preferably, the MTAM is hollow. More preferably, the MTAM is a single layer with hollow tubes. Preferably, the diameter of the tube ranges from about 30 µm to about 50 µm, about 35 µm to about 50 µm, about 40 µm to about 50 µm, about 30 µm to about 45 µm, about 30 µm to about 40 µm, about 35 µm to about 45 µm, or about 38 µm to about 42 µm. More preferably, the diameter of the tube is about 40 µm.

In some embodiments, the pore size of the MTAM ranges from about 20 nm to about 40 nm, about 25 nm to about 40 nm, about 30 nm to about 40 nm, about 20 nm to about 35 nm, about 20 nm to about 30 nm or about 28 nm to about 32 nm, in diameter. Preferably, the pore size of the MTAM is about 30 nm in diameter.

In some embodiments, the MTAM consists of biodegradable and/or bioabsorbable polymer selected from ethylene oxide, polyethylene oxide (PEO), ethylene glycol, polyethylene glycol (PEG), poly(lactic acid) (PLA), poly(glycolic acid) (PGA), poly(lactic-co-glycolic acid) (PLGA), poly (ethylene oxide) (PEO), nylon, polyesters, polyamides, poly (amic acids), polyimides, polyethers, polyketones, polyurethanes, polycaprolactones, polyacrylonitriles, polyaramides, conjugated polymers such as the electroluminescent polymer, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof. Preferably, the polymer is PLA.

The preparations of MTAM refer to K. L. Ou, C. S. Chen, L. H. Lin, J. C. Lu, Y. C. Shu, W. C. Tseng, J. C. Yang, S. Y. Lee, C. C. Chen, Membranes of epitaxial-like packed, super aligned electrospun micron hollow poly(L-lactic acid) (PLLA) fibers, Eur. Polym. J. 47 (2011) 882-892; J. S. Jang, Y. Cho, G. T. Jeong, S. K. Kim, Optimization of saccharification and ethanol production by simultaneous saccharification and fermentation (SSF) from seaweed, *Saccharina japonica*, Bioprocess Biosyst. Eng. 35 (2012) 11-18; J. C. Yang, S. Y. Lee, W. C. Tseng, Y. C. Shu, J. C. Lu, H. S. Shie, C. C. Chen, Formation of highly aigned, single-layered, hollow fibrous assemblies and the fabrication of large pieces of PLLA Membranes, Macromol. Mater. Eng. 297 (2012) 115-122; and L. C. Lin, Y. C. Shu, J. C. Yang, H. S. Shie, S. Y. Lee, C. C. Chen, Nano-porous poly-L-lactic acid microtube array membranes, Curr. Nanosci. 10 (2014) 227-234.

The invention uses a highly porous MTAM to immobilize yeast cells for bioethanol fermentation, a first in bioethanol production. MTAMs have structure similar but superior to hollow fibers and are developed using coaxial electrospinning. Compared with a typical hollow fiber, MTAMs are 1-2 orders smaller in diameter and >2 orders thinner in the tube wall; most strikingly, they can self-assemble into a single membrane sheet. MTAMs are further functionalized by creating nanopores on the surface using a pore-forming agent and followed by a leaching out process. With these structural characteristics, MTAMs provide a large surface area per volume and short diffusion distances with a self-supported barrier function. They are easily manipulated and low in cost. MTAMs serve as an excellent substrate to immobilize yeast for fermentation processes in an industrial scale.

In one aspect, the invention provides a method for bioethanol fermentation, comprising the following steps:
(a) immobilizating about $10^7$ to about $10^9$ cell numbers (CFU/mL) of yeast cells in MTAM by in situ preparation or siphon preparation to encapsulate the yeast cells into the MTAM with more than 60% encapsulation efficiency; and
(b) fermenting a sugar with the resulting MTAM to produce ethanol by batch fermentation.

Preferably, the cell number of the yeast cells is about $10^8$ CFU/mL.

Preferably, the sugar is glucose, fructose or sucrose. More preferably, the sugar is glucose at a concentration ranging from about 40 g/L to about 60 g/L. More preferably, the glucose is at a concentration of about 50 g/L.

Preferably, the batch fermentation is repeated-batch fermentation. More preferably, the repeated-batch fermentation is from 2 to 7 or 2 to 6 batches. More preferably, the repeated-batch fermentation is from 3 to 5 batches.

The embodiments of encapsulation efficiency and MTAM are described herein.

The invention optimizes the conditions to prepare MTAM-immobilized cells and evaluates their potential for batch bioethanol fermentation.

EXAMPLE

Materials and Methods
Source of *K. marxianus*

*K. marxianus* (BCRC 21363) was purchased from Bioresources Collection and Research Center (BCRC) in Hsinchu, Taiwan.

The Preparation of PLLA MTAM-Immobilized *K. marxianus*

The *K. marxianus* was cultured in a YPD medium (1% yeast extract, 2% bactopeptone, and 2% dextrose) at 42° C. to reach a cell density of $10^8$ and $10^9$ cfu/mL for immobilization. Materials used were PLLA (BioTechOne, Taiwan), polyethylene glycol/polyethylene oxide (PEG/PEO; Sigma-Aldrich), N,N-dimethyl formamide (DMF; Tedia, USA), and dichloromethane (DCM; Mallinckrodt, USA). To prepare the electrospinning dopes, PLLA was dissolved in mixed DCM/DMF (8/2) solvents at room temperature to obtain a 10% solution. PEG was added to the PLLA solution to obtain PEG/PLLA (30/70) solutions, as described previously.

An electrostatics charger (ChargeMaster, Simco-Ion, Alameda, Calif., USA) or a high voltage power supply unit (You-Shang Co., Fongshan city, Taiwan) was used as the source of electrostatics. Typically, electrospinning was performed by delivering the PLLA (shell) and PEG (core) solutions through a house-made co-axial spinneret with a syringe pump (KDS-100, KD Scientific, Holliston, Mass., USA) at the rate of 4-9 mL/h, with 5-7 kV applied voltage and 3-5 cm distance to a rotating drum collector. All electrospinning procedures were performed in a chamber at a relative humidity of 50±5% and a temperature of 25±1° C. Nano-porous PLLA MTAMs were obtained by washing to remove the core component of PEG, followed by drying. In situ preparation of yeast-containing PLLA MTAM was accomplished by using typical MTAM electrospinning process with similar parameters to those described above, with inner solution of mixed solution of yeast cell (cell density of $10^8$ mL$^{-1}$ and $10^9$ mL$^{-1}$) medium solution and PEG solution (1:9 in volume). The obtained MTAM samples were then cut into the dimensions of 3 cm×0.5 cm×0.0004 cm and both ends sealed by a heated metal plated. The siphoned yeast cell-containing PLLA MTAM was prepared by simply placing one open end of dried PLLA-MTAM into a fixed volume (10 µL) of yeast cell-medium solution (cell density of $10^8$ mL$^{-1}$ and $10^9$ mL$^{-1}$). After the capillary force siphoned the solution up throughout he MTAM, both ends were sealed by a heated metal plate.

The Stability Test of PLLA MTAM at Various Rpm and Ethanol Concentrations

The PLLA MTAMs were made as described previously and stored in 0.1% (w/v) peptone water at 4° C. For the stability test of PLLA MTAM at various ethanol concentrations, the prepared MTAMs were placed into ethanol solution at a concentration of 3%, 6%, 9%, 12%, and 15% (v/v), individually, at room temperature. The PLLA MTAM structure at each ethanol concentration was observed by naked eye and microscope for any breakage. For the stability test of PLLA MTAM, the prepared PLLA MTAMs were incubated in 0.1% (w/v) peptone water at 100, 200, 300, 400 and 500 rpm, individually, at room temperature. The PLLA MTAM structure at each ethanol concentration was observed by naked eye and microscope for any breakage.

Analysis of Encapsulation Efficiency

The PLLA MTAM-immobilized *K. marxiansu* was torn by using scissors and soaked in 0.1% (w/v) peptone. The mixture was thoroughly vortexed to release the immobilized cells into the peptone. The mixture was then diluted and plated out onto YPD plates and the plates were incubated at 42° C. for 24 h. The colonies were calculated to obtain the actual cell counts of the immobilized yeasts. The actual cell counts were divided by the theoretical cell counts of the immobilized yeast to obtain the encapsulation efficiency.

Batch and Repeated-Batch of Bioethanol Fermentation Using Immobilized *K. marxinaus*

For bioethanol fermentation, the PLLA MTAM-immobilized *K. marxianus* was placed into 100 mL of YPD medium containing 5% glucose (1% yeast extract, 2% bactopeptone, and 5% glucose) at 42° C. with a shaking of 200 rpm. The glucose usage and ethanol production in batch fermentation were monitored at 0, 6, 9, 12, 15 and 24 h. by using HPLC analysis. The optimum batch fermentation time enabling maximum ethanol production was observed and applied in repeated batch fermentation. Subsequently repeated batch bioethanol fermentation was accomplished with the same growth conditions as batch fermentation. At the end of each fermentation cycle, the PLLA MTAM-immobilized *K. marxianus* cells were washed with sterile peptone water and then transferred to the same volume of fresh YPD medium containing 5% glucose for the next cycle of fermentation. The cycles were repeated over and over until the production of bioethanol was no longer efficient. The glucose and bioethanol fermentation were measured at 0, 3, 6, 9 12 h during each cycle of fermentation. The parameters for bioethanol fermentation are shown in $C_{EtOH}$ (ethanol concentration), r $P_{EtOH}$ (initial ethanol production rate) and Max. $Y_{P/S}$ (maximum ethanol yields) [5]. $C_{EtOH}$ (g/L) is the maximum ethanol concentration to be achieved during fermentation; r $P_{EtOH}$ (g/L h) is $C_{EtOH}$ divided by the time (h) consumed to reach $C_{EtOH}$; Max. $Y_{P/S}$ (g/g) is obtained by dividing total produced ethanol during fermentation.

Analyses of Glucose and Ethanol Using HPLC

The glucose (g) and ethanol (g) were all analyzed using an Aminex HPX-87H column (Bio-Rad, Sunnyvale, Calif., USA), along with a refractive index detector with a 5 mM $H_2SO_4$ eluent at a flow rate of 0.6 mL/min at 60° C. All the tested samples were filtered through a 0.22 µm membrane filter prior to the HPLC analysis.

Statistical Analysis

Data were analyzed statistically using SPSS Version 12.0 (SPSS Inc., Chicago, Ill., USA). One-way analysis of variance (ANOVA) was used to determine statistical differences between sample means, with the level of significance set at P<0.05. Multiple comparisons of means were done by Tukey test. All data are expressed as mean±SD.

Example 1 Encapsulation of *K. marxianus* in PLLA MTAM

The scanning electron microscope (SEM) section image of MTAM is shown in FIG. 1(*a*). MTAM consists of a single layer of hollow tubes with a diameter of approximately 40 µm and a hollow tube wall pore diameter of approximately 30 nm. Free *K. marxianus* cells and MTAM-immobilized *K. marxianus* cells are shown in FIGS. 1(*b*) and (*c*). PLLA-MTAM entrapped the yeast cells for immobilization to obtain high biomass loadings in fermentation. Enantiomerically, pure PLLA is a semicrystalline polymer with a glass transition temperature of approximately 55° C. and a melting point of approximately 180° C. (*Prog. Polym. Sci.* 27 (2002) 1123-1163), suggesting that PLLA-MTAM is thermostable at all known bioethanol fermentation temperatures. Furthermore, PLLA is insoluble in water and its solubility in solvents is highly dependent on the molar mass and degree of crystallinity (*Prog. Polym. Sci.* 27 (2002) 1123-1163).

Example 2 Effects of Ethanol and Agitation on the Stability of MTAM

To determine the effect of agitation and ethanol, MTAM-immobilized *K. marxianus* was incubated at different rpm settings and ethanol concentrations. As shown in Table 1, MTAM retained a consistent solidity at 3%, 6%, 9%, 12%, and 15% (v/v) ethanol for more than 5 weeks (840 h) (data not shown). Our data indicated that MTAM was stable at 15% (v/v) ethanol for more than 840 h and that cell immobilization may be applicable for repeated-batch and continuous fermentations. The effect of agitation (100, 200, 300, 400, and 500 rpm) on MTAM was determined using 2 different methods, a rotary shaker and a fermenter with an impeller. As shown in Table 1, MTAM started to tear at an incubation time of 72-96 h on a rotary shaker at an rpm of 200. As the rpm was decreased, the time required for any tear to appear on MTAM was increased. At the rpm settings of 50 and 100, MTAM showed no tearing within 600 h (25 days). MTAM showed no obvious tearing at 100 rpm for up to 60 h and at 200 rpm for up to 36 h. The data suggested that the current PLLA-MTAM was applicable for anaerobic and aerobic fermentation with shaking.

TABLE 1

The effects of agitation and shaking on MTAM

| | Shaking incubator (rpm) | | | | |
|---|---|---|---|---|---|
| | 0 | 50 | 100 | 150 | 200 |
| Breakage time (h) | — | >600 | >600 | 144-168 | 72-96 |

| | Agitation in fermentor (rpm) | | | | |
|---|---|---|---|---|---|
| | 0 | 100 | 200 | 300 | 400 | 500 |
| Breakage time (h) | — | 60 | 36 | 12 | 12 | 12 |

Example 3 Effects of Encapsulation Methods and Cell Numbers on Encapsulation Efficiency We evaluated the encapsulation efficiency of yeast *K. marxianus* for 2 encapsulation methods, in situ and siphon preparations. As shown in Table 2, encapsulation of $10^8$ yeast cells using the in situ and siphon methods showed encapsulation efficiencies of 70.0±2.0% and 67.0±15.0%, respectively. The 2 methods showed similar encapsulation efficiencies at a cell density of $10^8$. Our encapsulation efficiency data suggested that the *K. marxianus* cells survived the process of electrospinning.

TABLE 2

The effects of encapsulation methods and cell numbers on encapsulation efficiency.

| | Encapsulation efficiency (%) | |
|---|---|---|
| Cell numbers (CFU/ml) | in situ preparation | Siphone |
| $10^8$ | 70 ± 2.0% | 67 ± 15.0% |

Data are expressed as mean ± SD (n = 3).

Example 4 Effects of Encapsulation Methods and Porosity of MTAM on Yeast Growth and Batch Bioethanol Fermentation FIG. 1(a) shows that MTAM was a single layer with a hollow tube diameter of approximately 40 μm, and a nanopore diameter of approximately 30 nm on the surface of each hollow tube, allowing simple sugars, alcohol, and other small molecules to diffuse in and out. In order to determine whether greater porosity on the surface of the tube would accelerate sugar consumption and ethanol production, possibly because of greater diffusion of sugars and ethanol across the barrier, we used 10% (v/v) pore-forming agent polyethylene glycol in PLLA-MTAM preparation to produce greater porosity with nanopore diameters of 0.31±0.08 μm on the surface of the MTAM hollow tube wall. As shown in Table 3, the in situ preparation of MTAM-immobilized *K. marxianus* with greater porosity showed a $C_{EtOH}$ of 8.76±0.07 g/L, r $P_{EtOH}$ of 0.73±0.01 g/Lh, and maximum $Y_{P/S}$ of 0.43±0.01$^a$ (g/g) during bioethanol fermentation, which were better than the corresponding values for the original MTAM. With regard to MTAM-immobilized *K. marxianus* with greater porosity prepared by the siphon method, there were no obvious differences compared with the original MTAM in the parameters of bioethanol fermentation. The encapsulation efficiency using this method showed a relatively higher standard deviation, suggesting a large discrepancy between the number of cells involved in each encapsulation of the original MTAM and MTAM with a greater porosity. We used 10% (v/v) polyethylene glycol to create MTAM-immobilized *K. marxianus* for the rest of the study.

TABLE 3

The effect of porosity of MTAM on bioethanol fermentation in 12 h.

| | $C_{EtOH}$ (g/L) | r $P_{EtOH}$ (g/Lh) | Max. $Y_{P/S}$ (g/g) |
|---|---|---|---|
| In situ preparation | | | |
| MTAM with greater porosity | 8.76 ± 0.07$^a$ | 0.73 ± 0.01$^a$ | 0.43 ± 0.01$^a$ |
| MTAM | 7.86 ± 0.08$^b$ | 0.66 ± 0.01$^b$ | 0.39 ± 0.01$^b$ |
| Siphon | | | |
| MTAM with greater porosity | 8.13 ± 0.39$^b$ | 0.67 ± 0.03$^b$ | 0.39 ± 0.02$^b$ |
| MTAM | 7.89 ± 0.10$^b$ | 0.66 ± 0.01$^b$ | 0.39 ± 0.01$^b$ |

$C_{EtOH}$ (Ethanol concentration);
r $P_{EtOH}$ (Initial ethanol production rate);
Max. $Y_{P/S}$ (Maximum ethanol yields).
Data are expressed as mean ± SD (n = 3).
Different letters in column show significant differences (p < 0.05).

Example 5 Sugar Usage and Bioethanol Fermentation of Glucose Using Free and MTAM-Immobilized *K. marxianus*

Figure 2:
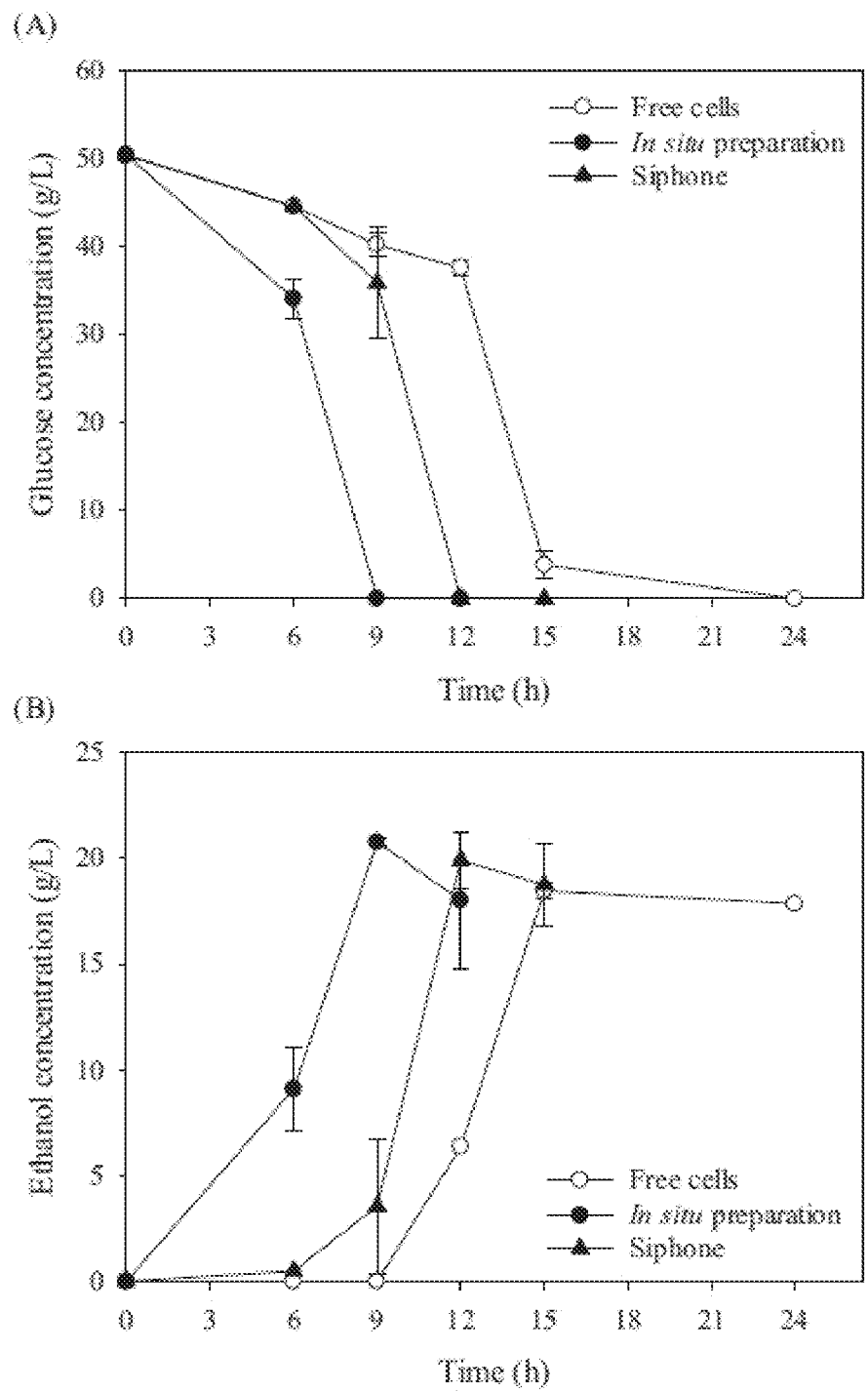
FIGS. 2 (a) and (b) show the (a) sugar usage and (b) bioethanol production in batch fermentation of YPD using free and immobilized *K. marxianus*. Batch fermentation of YPD medium containing 5% (w/v) glucose was incubated at 42° C. with a shaking of 200 rpm. Data are expressed as mean f SD (n=3).

The bioethanol fermentation of YPD by free and MTAM-immobilized *K. marxianus* is shown in FIG. 2. The starting cell density of free and MTAM-immobilized *K. marxianus* in fermentation were kept constant at $10^5$ CFU/mL. The results showed that compared with free cells, batch fermentation with yeast cells immobilized in MTAM required less fermentation time to convert glucose to bioethanol. Glucose at a concentration of 50 g/L was consumed by the free cells in 24 h, whereas MTAM-immobilized cells prepared by the in situ and siphon methods depleted glucose in 9 h and 12 h, respectively, indicating that MTAM-immobilized *K. marxianus* improved efficiency.

A maximum bioethanol concentration of 18.46 g/L was obtained from fermentation using free cells after 15 h. The immobilized yeast cells in MTAM from the in situ and siphon preparations showed maximum bioethanol concentrations of 20.7 g/L (9 h) and 19.9 g/L (12 h), which were 10% and 8% higher than that of free cells, respectively. In this study we used MTAM-immobilized *K. marxianus* for batch fermentation and improved ethanol productivity by 8-10% compared with free cells depending on the preparation method used.

Example 6 Repeated-Batch Bioethanol Fermentation of YPD Using MTAM-Immobilized *K. marxianus*

Figure 3:
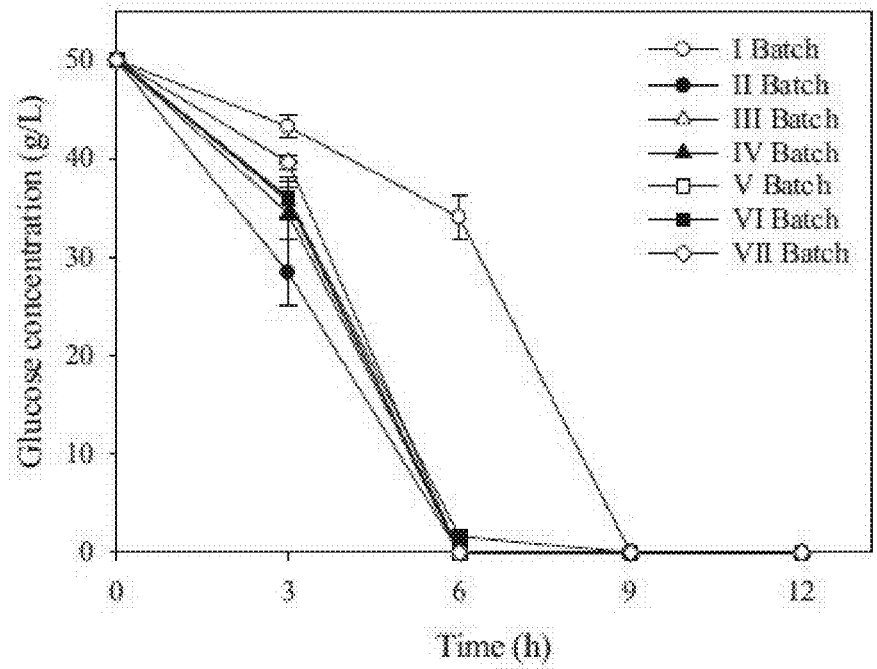
FIGS. 3 (a) and (b) show the (a) sugar usage and (b) bioethanol production in repeated batch fermentation of YPD using immobilized *K. marxianus*. Repeated-batch fermentation of YPD medium containing 5% (w/v) glucose was incubated at 42° C. with a shaking of 200 rpm. Data are expressed as mean±SD (n=3).
Figure 3:
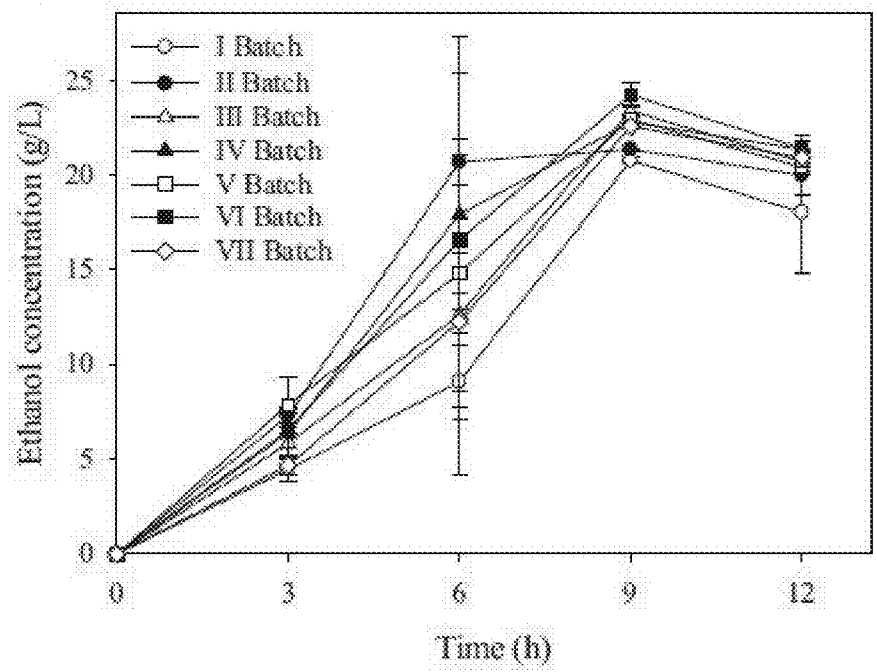

Glucose consumption and ethanol production in repeated-batch fermentation using MTAM-immobilized *K. marxianus* were studied as a function of time (FIG. 3). The first batch of MTAM-immobilized cells consumed 17 g/L of the starting 50 g/L glucose (34%) at 6 h. From batch II to VII, the same MTAM was reused and each batch consumed more than 95% glucose at 6 h (FIG. 3(a)). Furthermore, all the batches, including the first batch, consumed all the glucose in 9 h. As a result, the highest ethanol concentration in all batches was obtained at 9 h of fermentation, which started to decrease at 12 h, possibly because of ethanol oxidation for metabolism when glucose was unavailable. The standard deviations of ethanol concentration at 6 h for all the batches were greater than those at any other time point, suggesting that some immobilized MTAMs could achieve maximum ethanol production before 9 h. Our attempt to encapsulate *K. marxianus* in MTAM for repeated-batch bioethanol fermentation successfully reduced the processing cost of inoculum preparation, and accelerated glucose consumption and ethanol production. Evaluation of the kinetic parameters for ethanol production using free cells in fermentation and MTAM-immobilized *K. marxianus* in repeated-batch fermentation is shown in Table 4. As expected, MTAM-immobilized cells in every batch showed improved performance in terms of sugar consumption and ethanol production compared with free cells. Bioethanol fermentation using free *K. marxianus* cells showed a glucose consumption of 93%, $C_{EtOH}$ of 18.46±0.38 g/L, maximum $Y_{P/S}$ of 0.40±0.002 g/g. and r $P_{EtOH}$ of 1.23±0.02 g/L h at 15 h. For the immobilized cells, the first batch showed the lowest ethanol productivity in $C_{EtOH}$ (20.78±0.16 g/L), maximum $Y_{P/S}$ (0.42±0.003 g/g), and r $P_{EtOH}$ (2.31±0.02 g/L h) at 9 h. In subsequent batches, ethanol productivity increased gradually until batch VI, and the $C_{EtOH}$, maximum $Y_{P/S}$, and r $P_{EtOH}$ obtained in batches III, IV, V, and VI were higher than those of the first 2 batches. The immobilized cells prepared by the in situ preparation gave a maximum $C_{EtOH}$ of 24.23±0.63 g/L, maximum $Y_{P/S}$ of 0.48±0.012 g/g, and r $PO_H$ of 2.69±0.07 g/L for the 6 cycles of repeated-batch fermentation with a slight reduction in the last cycle of fermentation. Ethanol productivity started to decrease in batch VII, possibly because of aging yeast cells; these in physical properties, cell encapsulation efficiency and immobilization technology was performed, and our data indicated that MTAM-immobilized yeasts showed great potential in repeated-batch and continuous bioethanol fermentation. The invention first introduce this cell immobilization technique to bioethanol fermentation.

TABLE 4

Evaluation of kinetic parameters for ethanol production by free cells in batch fermentation and MTAM-encapsulated *K. marxianus* in repeated-batch fermentation.

| Batch | Substrate utilization (%) | $C_{EtOH}$ (g/L) | Max/$Y_{P/S}$ (g/g) | r $P_{EtOH}$ (g/Lh) | Time (h) |
|---|---|---|---|---|---|
| Free cells | 93 | 18.46 ± 0.38$^b$ | 0.40 ± 0.002$^c$ | 1.23 ± 0.02$^d$ | 15 |
| I | 100 | 20.78 ± 0.16$^a$ | 0.42 ± 0.003$^d$ | 2.31 ± 0.02$^c$ | 9 |
| II | 100 | 21.36 ± 0.04$^d$ | 0.43 ± 0.001$^d$ | 2.37 ± 0.04$^c$ | 9 |
| III | 100 | 23.39 ± 0.36$^b$ | 0.47 ± 0.007$^{ab}$ | 2.60 ± 0.04$^{ab}$ | 9 |
| IV | 100 | 22.79 ± 0.30$^c$ | 0.46 ± 0.006$^{bc}$ | 2.53 ± 0.03$^b$ | 9 |
| V | 100 | 22.94 ± 0.21$^{bc}$ | 0.46 ± 0.004$^{bc}$ | 2.55 ± 0.02$^b$ | 9 |
| VI | 100 | 24.23 ± 0.63$^d$ | 0.48 ± 0.012$^a$ | 2.69 ± 0.07$^a$ | 9 |
| VII | 100 | 22.57 ± 0.15$^c$ | 0.45 ± 0.003$^c$ | 2.51 ± 0.02$^b$ | 9 |

$C_{EtOH}$ (Ethanol concentration);
r $P_{EtOH}$ (Initial ethanol production rate);
Max. $Y_{P/S}$ (Maximum ethanol yields);
Data are expressed as mean ± SD (n = 3).
Different letters in column show significant differences (p < 0.05).

What is claimed is:

1. A composition comprising a combination of yeast cells and a porous microtube array membrane (MTAM), wherein the yeast cells are immobilized in the MTAM and wherein the yeast encapsulation efficiency is more than 60%.

2. The combination of claim 1, wherein the yeast cell is *Kluyveromyces marxianus, Kluyveromyces lactis, Kluyveromyces lipolytica, Saccharomyces cerevisiae* or *Schizosaccharomyces pombe*.

3. The combination of claim 1, wherein the MTAM is highly aligned and closely packed fiber assembly and wherein the fibers are packed together to form a single layer and the orientation of the fibers is no larger than +/−5°.

4. The combination of claim 1, wherein the MTAM is a single layer with hollow tubes.

5. The combination of claim 4, wherein the diameter of the tube ranges from about 30 μm to about 50 μm.

6. The combination of claim 1, wherein the pore size of the MTAM ranges from about 20 nm to about 40 nm.

7. The combination of claim 1, wherein the MTAM consists of biodegradable and/or bioabsorbable polymer selected from ethylene oxide, polyethylene oxide (PEO), ethylene glycol, polyethylene glycol (PEG), poly(lactic acid) (PLA), poly(glycolic acid) (PGA), po 1 y(1 actic-co-glycolic acid) (PLGA), poly(ethylene oxide) (PEO), nylon, polyesters, polyamides, poly(amic acids), polyimides, polyethers, polyketones, polyurethanes, polycaprolactones, polyacrylonitriles, polyaramides, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof.

8. The combination of claim 1, wherein the MTAM is PLA.

9. A method for bioethanol fermentation, comprising the following steps:
 (a) immobilizing about $10^7$ to about $10^9$ cell numbers (CFU/mL) of yeast cells in MTAM by in situ preparation or siphon preparation to encapsulate the yeast cells into the MTAM with more than 60% encapsulation efficiency; and
 (b) fermenting a sugar with the resulting MTAM to produce ethanol by batch fermentation.

10. The method of claim 9, wherein the cell number of the yeast cells in (a) is about $10^8$ CFU/mL.

11. The method of claim 9, wherein the sugar is glucose, fructose or sucrose.

12. The method of claim 9, wherein the sugar is glucose at a concentration ranging from about 40 g/L to about 60 g/L.

13. The method of claim 9, wherein the batch fermentation is repeated-batch fermentation.

14. The method of claim 13, wherein the repeated-batch fermentation is from 2 to 7 batches.

* * * * *